(12) United States Patent
Gan et al.

(10) Patent No.: US 9,481,757 B2
(45) Date of Patent: *Nov. 1, 2016

(54) OXAZOLIDONE RING CONTAINING ADDUCTS

(71) Applicant: Blue Cube IP LLC, Midland, MI (US)

(72) Inventors: Joseph Gan, Strasbourg (FR); Emile C. Trottier, Renchen (DE)

(73) Assignee: Blue Cube IP LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/538,281

(22) Filed: Nov. 11, 2014

(65) Prior Publication Data

US 2015/0073115 A1    Mar. 12, 2015

Related U.S. Application Data

(63) Continuation of application No. 13/514,124, filed as application No. PCT/US2010/003218 on Dec. 20, 2010, now Pat. No. 8,912,291.

(60) Provisional application No. 61/289,123, filed on Dec. 22, 2009.

(51) Int. Cl.

| | |
|---|---|
| *C08G 18/00* | (2006.01) |
| *C08G 59/22* | (2006.01) |
| *C08G 59/40* | (2006.01) |
| *C08G 59/42* | (2006.01) |
| *C08G 59/50* | (2006.01) |
| *C08L 63/00* | (2006.01) |
| *C08L 75/00* | (2006.01) |
| *C09D 179/00* | (2006.01) |
| *C08G 73/06* | (2006.01) |
| *C09D 5/03* | (2006.01) |
| *C09D 163/00* | (2006.01) |
| *C09D 175/00* | (2006.01) |
| *C08L 79/00* | (2006.01) |

(52) U.S. Cl.
CPC ............. *C08G 18/003* (2013.01); *C08G 59/22* (2013.01); *C08G 59/223* (2013.01); *C08G 59/226* (2013.01); *C08G 59/4014* (2013.01); *C08G 59/4028* (2013.01); *C08G 59/42* (2013.01); *C08G 59/50* (2013.01); *C08G 73/06* (2013.01); *C08L 63/00* (2013.01); *C08L 75/00* (2013.01); *C08L 79/00* (2013.01); *C09D 5/03* (2013.01); *C09D 163/00* (2013.01); *C09D 175/00* (2013.01); *C09D 179/00* (2013.01); *C08G 2150/20* (2013.01); *C08L 2203/02* (2013.01)

(58) Field of Classification Search
CPC  C07D 263/20; C07D 263/22; C08G 18/003; C08G 18/58; C08G 59/22; C08G 59/223; C08G 59/226; C08G 59/4028; C08G 73/06; C08G 59/4014; C08G 59/42; C08G 59/50; C08G 2150/20; C08L 63/00; C08L 2203/02; C08L 79/00; C08L 75/00; C09D 5/03; C09D 163/00; C09D 175/00; C09D 179/00

See application file for complete search history.

(56) References Cited

U.S. PATENT DOCUMENTS

| | | | | |
|---|---|---|---|---|
| 4,022,721 | A | * | 5/1977 | Ashida .......................... 521/108 |
| 4,658,007 | A | * | 4/1987 | Marks et al. ................... 528/55 |
| 5,112,932 | A | | 5/1992 | Koenig et al. |
| 5,314,720 | A | | 5/1994 | Gan et al. |
| 5,545,697 | A | | 8/1996 | Uchida |
| 6,613,839 | B1 | | 9/2003 | Gan et al. |
| 8,912,291 | B2 | * | 12/2014 | Gan et al. ...................... 525/452 |

FOREIGN PATENT DOCUMENTS

| | | | |
|---|---|---|---|
| CA | 2038786 | * | 9/1991 |
| EP | 0113233 | | 7/1984 |
| EP | 0113575 | | 7/1984 |
| WO | 02073772 | | 9/2002 |
| WO | 2009045835 | | 4/2009 |

OTHER PUBLICATIONS

International Search Report and Written Opinion from related PCT application PCT/US2010/003218 dated May 30, 2011, 12 pages.
Written Opinion of the International Preliminary Examining Authority from related PCT application PCT/US2010/003218 dated Jan. 13, 2012, 5 pages.

* cited by examiner

*Primary Examiner* — Rabon Sergent
(74) *Attorney, Agent, or Firm* — Polsinelli PC

(57) ABSTRACT

Embodiments include oxazolidone ring containing adducts obtainable by combining an aliphatic epoxy compound, an aromatic epoxy compound, and a diisocyanate. Embodiments further include a curable powder coating composition including a resin component and a hardener component, where the resin component includes the oxazolidone ring containing adduct.

3 Claims, No Drawings

OXAZOLIDONE RING CONTAINING ADDUCTS

This application is a Continuation Application of U.S. National Stage Application 13/514,124, filed Jun. 6, 2012 and issued as U.S. Pat. No. 8,912,291 on Dec. 16, 2014, which claims benefit to International Application Number PCT/US2010/003218, filed Dec. 20, 2010 and published as WO 2011087486 on Jul. 21, 2011, which claims priority to U.S. Provisional Application 61/289,123 filed Dec. 22, 2009, the entire contents of which are incorporated herein by reference in its entirety.

FIELD OF DISCLOSURE

The present disclosure relates to adducts, and in particular oxazolidone ring containing adducts.

BACKGROUND

Epoxy systems consist of two components that can chemically react with each other to form a cured epoxy, which is a hard, inert material. The first component is an epoxy resin and the second component is a curing agent, sometimes called a hardener. Epoxy resins are substances or mixtures that contain epoxide groups. The hardener includes compounds that are reactive with the epoxide groups of the epoxy resins.

The epoxy resins can be crosslinked, also referred to as curing, by the chemical reaction of the epoxide groups and the compounds of the hardener. This curing converts the epoxy resins, which have a relatively low molecular weight, into relatively high molecular weight materials by chemical addition of the compounds of the hardener.

Epoxy systems are used in a great variety of applications, including coatings. Coatings are used to treat surfaces to protect against corrosion and other forms of degradation caused by use and/or the environment. The types of surfaces treated include concrete, metal, and other surfaces.

Some epoxy systems used for coatings are liquid based systems. Some of the liquid based systems contain volatile organic solvents. Volatile organic solvents are becoming less desirable for some applications and use of these liquid based systems has been curtailed. Some other liquid based systems are solvent free. The solvent free liquid based systems can require costly, non-standardized equipment for application of the coating. However, the solvent free liquid based systems, like other liquid based systems, have disadvantages including premixing, monitoring and maintenance of viscosity, and the possibility of running or sagging during and after application of the coating.

Some other epoxy systems used for coatings are solid based systems. Powder coatings are examples of solid based systems. Powder coatings can be formed when a solid epoxy resin, a solid hardener, and other elements, if desired, are combined by melting and extruded. The molten extrudate can be cooled and milled to a desired particle size for the particular application. The powder coating can be applied to an article via a spray gun, by exposing the article to a fluidized bed of the powder coating, or by another procedure. Following the application of the powder coating to the article the epoxy system is cured. The article thus coated.

There are many possible uses for powder coatings, and there are a great variety of characteristics that may desirable for particular applications.

SUMMARY

The present disclosure provides one or more embodiments of an oxazolidone ring containing adduct that is obtainable by combining an aliphatic epoxy compound, an aromatic epoxy compound, and a diisocyanate.

For one or more of the embodiments, the present disclosure provides a curable powder coating composition that includes a resin component and a hardener component. The resin component includes the oxazolidone ring containing adduct.

DETAILED DESCRIPTION

The present disclosure provides oxazolidone ring containing adducts, curable powder coating compositions, and products obtainable by curing the curable powder coating compositions that provide surprising characteristics that makes these adducts, compositions, and products useful for some applications. Examples of these applications include, but are not limited to, powder coatings, electrical laminates, electrical encapsulations, and composites.

For some of these applications it is advantageous to employ the oxazolidone ring containing adducts to help prevent sintering. Sintering is a time, temperature, and/or pressure dependent process whereby individual particles or flakes of an epoxy system fuse together to form a larger solid mass. While sintering is not a chemical reaction, sintering can make the epoxy system unusable for particular applications. For example, in powder coatings sintered epoxy resins are very difficult to evenly disperse which can result in an undesirable extrusion. Additionally, for applications where an epoxy resin is dissolved in a solvent a sintered epoxy resin will require a greater time to dissolve than a non-sintered epoxy resin. This greater time results because the larger solid mass of the sintered epoxy resin will have less available surface area than the non-sintered particles for the solvent to contact. The disclosed oxazolidone ring containing adducts and curable powder coating compositions that include the oxazolidone ring containing adducts will not sinter at standard atmospheric pressure while maintained at temperature is less than or equal to 25° C. under dry conditions.

The oxazolidone ring containing adducts are obtainable by combining separate compounds. Adduct refers to a compound that is formed from a combination of two or more other compounds. The combination can be a chemical reaction. The chemical reaction can be an addition reaction. An addition reaction is a chemical reaction of two or more compounds, resulting in a single reaction product containing all atoms of all compounds. Compound refers to a substance composed of atoms or ions of two or more elements in chemical combination.

An oxazolidone ring is an organic compound containing both nitrogen and oxygen in a five-membered ring. Herein, the separate compounds that are combined to obtain the oxazolidone ring containing adducts include aliphatic epoxy compounds, aromatic epoxy compounds, and diisocyanates. An epoxy compound is a compound in which an oxygen atom is directly attached to two adjacent or non-adjacent carbon atoms of a carbon chain or ring system.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to, glycidyl ethers of polyols, such as 1,4-butanediol diglycidyl ether, 1,6-hexanediol diglycidyl ether, a triglycidyl ether of glycerin, a triglycidyl ether of trimethylol propane, a tetraglycidyl ether of sorbitol, a hexaglycidyl ether of dipentaerythritol, a diglycidyl ether of polyethylene glycol, and a diglycidyl ether of polypropylene glycol; polyglycidyl ethers of polyether polyols obtained by adding one type, or two or more types, of alkylene oxide to aliphatic polyols such as propylene glycol, trimethylol propane, and glycerin; and diglycidyl esters of aliphatic long-chain dibasic acids. A combination of aliphatic epoxy compounds is employed for one or more embodiments.

Examples of aromatic epoxy compounds include, but are not limited to, glycidyl ether compounds of polyphenols, such as hydroquinone, resorcinol, bisphenol A, bisphenol F, 4,4'-dihydroxybiphenyl, novolac, tetrabromobisphenol A, 2,2-bis(4-hydroxyphenyl)-1,1,1,3,3,3-hexafluoropropane, and 1,6-dihydroxynaphthalene. A combination of aromatic epoxy compounds is employed for one or more embodiments.

A diisocyanate is a compound that has two isocyanate groups. Diisocyanates include aromatic diisocyanates and aliphatic diisocyanates. Examples of aromatic diisocyanates include, but are not limited to, 4,4'-diphenylmethane diisocyanate (MDI), toluene diisocyanate (TDI), xylene diisocyanate (XDI), and isomers thereof. Examples of aliphatic diisocyanates include, but are not limited to, hexamethylene diisocyanate (HMDI), isophorone diisocyanate (IPDI), 4,4'-methylenebis(cyclohexylisocyanate), trimethyl hexamethylene diisocyanate, and isomers thereof. A combination of diisocyanates is employed for one or more embodiments. For one or more embodiments, employing a diisocyanate having a greater isocyanate content, as compared to another diisocyanate having a relatively lesser isocyanate content, can help provide a relatively greater proportion of oxazolidone ring incorporation to molecular weight of the oxazolidone ring containing adducts.

The oxazolidone ring containing adducts are obtainable by combining the aliphatic epoxy compound, the aromatic epoxy compound, and the diisocyanate. A process for combining the aliphatic epoxy compound, the aromatic epoxy compound, and the diisocyanate can include a first stage and a second stage.

The first stage of the process can include incorporating oxazolidone rings into the aliphatic epoxy compounds of a first stage adduct. The aliphatic epoxy compounds can be 20 weight percent (wt %) to 60 wt % of a total weight of the oxazolidone ring containing adducts. The first stage of the process can include heating the aliphatic epoxy compounds to a temperature of 100 degrees Celsius (° C.) to 180° C. under a nitrogen atmosphere for a period of 30 minutes (min.) to 180 min.

The first stage of the process can include employing a catalyst suitable for incorporating oxazolidone rings into the aliphatic epoxy compounds. Examples of the catalyst include, but are not limited to, lithium compounds such as lithium chloride and butoxylithium; boron trifluoride complex salts; quaternary ammonium salts such as tetramethylammonium chloride, tetramethylammonium bromide, and tetramethylammonium iodide; tertiary amines such as dimethylaminoethanol, triethylamine, tributylamine, benzyldimethylamine, and N-methylmorpholine; phosphines such as triphenylphosphine; phosphonium compounds such as allyltriphenylphosphonium bromide, diallyldiphenylphosphonium bromide, ethyltriphenylphosphonium chloride, ethyltriphenylphosphonium iodide, tetrabutylphosphonium acetate-acetic acid complexes, tetrabutylphosphonium acetate, tetrabutylphosphonium chloride, tetrabutylphosphonium bromide, and tetrabutylphosphonium iodide; a combination of triphenylantimony and iodine; imidazols, including imidazol derivatives, such as 2-phenylimidazol and 2-methylimidazol; other compounds such as 1,8 diazabicyclo (5,4,0) undecene-7; a Lewis acid; and combinations thereof. Lewis acids include, but are not limited to, halides, oxides, hydroxides, and alkoxides of beryllium, zinc, cadmium, boron, aluminum, gallium, titanium, zirconium, antimony, tin, bismuth, iron, and cobalt; anhydrides thereof; and combinations thereof.

The catalyst can be included in an amount of 20 parts per million (ppm) to 5,000 ppm, based upon a total mass of the aliphatic epoxy compounds and the diisocyanates of the first stage of the process. However, for some applications the catalyst can be included in another amount. For one or more embodiments a combination of catalysts is employed. A mixture of the aliphatic epoxy compounds and the catalyst can be maintained at a temperature of from 100° C. to 180° C. under a nitrogen atmosphere.

The first stage of the process includes adding the diisocyanates to the mixture of the aliphatic epoxy compounds and the catalyst. The diisocyanates can be 10 wt % to 40 wt % of the total weight of the oxazolidone ring containing adducts. For one or more embodiments, the diisocyanates can be bifurcated into a first stage portion and a second stage portion, where the first stage portion is added during the first stage and the second stage portion is added during the second stage. A combination of the first stage portion and the second stage portion can be 10 wt % to 40 wt % of the total weight of the oxazolidone ring containing adducts.

A mixture containing the aliphatic epoxy compounds, the catalysts, and the diisocyanates can be maintained at a temperature of 150° C. to 180° C. under nitrogen atmosphere to obtain the first stage adduct. The first stage adducts include oxazolidone rings incorporated into the aliphatic epoxy compounds. The first stage adducts can have an epoxide equivalent weight (EEW) of 1300 grams/equivalent (g/eq) to 1600 g/eq. The first stage adducts can have a melt viscosity at 150° C. of 1 pascal second (Pa·s) to 10 Pa·s.

The second stage of the process includes adding the aromatic epoxy compounds to the first stage adducts. The aromatic epoxy compounds can be 20 wt % to 40 wt % of the total weight of the oxazolidone ring containing adducts. The second stage of the process can include heating a mixture of the first stage adducts and the aromatic epoxy compounds to a temperature of 100° C. to 180° C. under a nitrogen atmosphere.

The second stage of the process can include adding the second stage portion of the diisocyanates to the mixture of the first stage adducts and the aromatic epoxy compounds. A mixture containing the first stage adducts, the aromatic epoxy compounds, and second stage portion of the diisocyanates can be maintained at a temperature of 150° C. to 180° C. to obtain the oxazolidone ring containing adducts.

The oxazolidone ring containing adducts can have an EEW of 800 g/eq td 1300 g/eq, a melt viscosity at 150° C. of 2 Pa·s to 10 Pa·s, a glass transition temperature ($T_g$) of 40° C. to 55° C., and a softening point of 80° C. to 100° C.

For one or more of the embodiments, the present disclosure provides curable powder coating compositions that include a resin component and a hardener component, where the resin component includes the oxazolidone ring containing adduct obtainable by combining the aliphatic epoxy compound, the aromatic epoxy compound, and the diisocyanate, and the hardener component is selected from the group consisting of amines, anhydrides, and combinations thereof.

For one or more embodiments, the resin component can further include an additional epoxy compound. The additional epoxy compound can be selected from the group consisting of aliphatic epoxy compounds, aromatic epoxy compounds, alicyclic epoxy compounds, and combinations thereof. Examples of suitable aliphatic epoxy compounds and/or aromatic epoxy compounds are discussed herein.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to, hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate.

For one or more embodiments, where the resin component further includes the additional epoxy compound, the oxazolidone ring containing adducts are useful as a flexibilizer. Flexibilizers are compounds that chemically react with the resin component and/or the hardener component to become incorporated into a cured composition. Flexibilizers can vary the characteristics of the cured compositions for various applications. For example, employing a flexibilizer can help provide that the cured composition is less brittle than a cured composition that does not employ the flexibilizer. For these embodiments, the oxazolidone ring containing adducts can be from 5 wt % to 25 wt % of a total weight of the curable powder coating compositions.

The hardener component is selected from the group consisting of amines, anhydrides, carboxyl-functional polyesters, and combinations thereof. For one or more of the embodiments, the hardener component can include an amine. The amine is a compound that contains an N-H moiety. The amine is selected from the group consisting of aliphatic polyamines, arylaliphatic polyamines, cycloaliphatic polyamines, aromatic polyamines, heterocyclic polyamines, polyalkoxy polyamines, and combinations thereof.

Examples of aliphatic polyamines include, but are not limited to, dicydiamide (DICY), ethylenediamine (EDA), diethylenetriamine (DETA), triethylenetetramine (TETA), trimethyl hexane diamine (TMDA), hexamethylenediamine (NMDA), N-(2-aminoethyl)-1,3-propanediamine ($N_3$-Amine), N,N'-1,2-ethanediylbis-1,3-propanediamine ($N_4$-amine), and dipropylenetriamine. Examples of arylaliphatic polyamines include, but are not limited to, m-xylylenediamine (mXDA), and p-xylylenediamine. Examples of cycloaliphatic polyamines include, but are not limited to, 1,3-bisaminocyclohexylamine (1,3-BAC), isophorone diamine (IPDA), and 4,4'-methylenebiscyclohexanamine. Examples of aromatic polyamines include, but are not limited to, m-phenylenediamine, diaminodiphenylmethane (DDM), and diaminodiphenylsulfone (DDS). Examples of heterocyclic polyamines include, but are not limited to, N-aminoethylpiperazine (NAEP), and 3,9-bis(3-aminopropyl) 2,4,8,10-tetraoxaspiro(5,5)undecane. Examples of polyalkoxy polyamines include, but are not limited to, 4,7-dioxadecane-1,10-diamine; 1-propanamine; (2,1-ethanediyloxy)bis(diaminopropylated diethylene glycol)(ANCAMINE® 1922A); poly(oxy(methyl-1,2-ethanediyl)); alpha-(2-aminomethylethyl)omega-(2-aminomethylethoxy) (JEFFAMINE® D-230, D-400); triethyleneglycoldiamine and oligomers (JEFFAMINE® XTJ-504, JEFFAMINE® XTJ-512); poly(oxy(methyl-1,2-ethanediyl)),alpha,alpha'-(oxydi-2,1-etha nediyl)bis(omega-(aminomethylethoxy)) (JEFFAMINE® XTJ-511); bis(3-aminopropyl)polytetrahydrofuran 350; bis(3-aminopropyl)polytetrahydrofuran 750; poly(oxy(methyl-1,2-ethanediyl)); a-hydro-w-(2-aminomethylethoxy) ether with 2-ethyl-2-(hydroxymethyl)-1,3-propanediol (JEFFAMINE® T-403); and diaminopropyl dipropylene glycol.

For one or more of the embodiments, the hardener component can include an anhydride. The anhydride is a compound having two acyl groups bonded to the same oxygen atom. The anhydride can be symmetric or mixed. Symmetric anhydrides have identical acyl groups. Mixed anhydrides have different acyl groups. The anhydride can be selected from the group consisting of aromatic anhydrides, alicyclic anhydrides, aliphatic anhydride and combinations thereof.

Examples of aromatic anhydrides include, but are not limited to, 3,3',4,4'-benzophenonetetracarboxylic dianhydride, styrene-maleic acid anhydride copolymers, and pyromellitic anhydride. Examples of alicyclic anhydrides include, but are not limited to, methyltetrahydrophthalic anhydride; tetrahydrophthalic anhydride; methyl nadic anhydride; hexahydrophthalic anhydride; and methylhexahydrophthalic anhydride. Examples of aliphatic anhydrides include, but are not limited to, propionic anhydride and acetic anhydride.

For one or more of the embodiments, the hardener component can include a carboxyl-functional polyester. Examples of the carboxyl-functional polyester include, but are not limited to, carboxyl-functional polyesters prepared from neopentyl glycol and/or 1,3-propanediol.

For one or more of the embodiments, the curable powder coating composition further includes a polyester resin. Embodiments including the polyester resin may be referred to as a hybrid. The polyester resin can have a glass transition temperature of −5° C. to 80° C. and a number average molecular weight of 5,000 to 30,000. The polyester resin is less than 60 wt % of a total weight of the curable powder coating composition. The polyester resin is obtainable by reacting an acid component with an alcohol component in an esterification reaction and/or an ester exchange reaction.

The acid component can include an aromatic dicarboxylic acid, an aliphatic dicarboxylic acid, a monocarboxylic acid, and combinations thereof. The alcohol component can include a dialcohol.

Examples of the aromatic dicarboxylic acid include, but are not limited to, terephthalic acid, isophthalic acid, phthalic acid, naphthalene dicarboxylic acid, lower alkyl esters thereof, and acid anhydrides thereof. Examples of the aliphatic dicarboxylic acid include, but are not limited to, adipic acid, sebacic acid, azelaic acid, succinic acid, fumaric acid, maleic acid, 1,6-cyclohexane dicarboxylic acid, lower alkyl esters thereof, and acid anhydrides thereof. An example of the monocarboxylic acid includes, but is not limited to, p-t-butyl benzoic acid. Examples of the dialcohol include, but are not limited to, ethylene glycol, propylene glycol, 1,2-propane diol, 1,3-propane diol, 1,3-butane diol, 1,4-butane diol, neopentyl glycol, 1,5-pentane diol, 1,6-hexane diol, 3-methylpentane diol, diethylene glycol, 1,4-cyclohexane dimethanol, 3-methyl-1,5-pentane diol, 2-methyl-1,3-propane diol, 2,2-diethyl-1,3-propane diol, 2-butyl-2-ethyl-1,3-propane diol, xylylene glycol, hydrogenated bisphenol A, and ethylene oxide or propylene oxide adducts of bisphenol A.

For one or more embodiments, the curable powder coating compositions include the Lewis acid, as discussed herein. Employing the Lewis acid can be used to increase a gel time of the curable powder coating compositions. When the gel time is increased it is possible to use a greater concentration of catalyst, as compared to embodiments not including the Lewis acid. The greater concentration of catalyst can help provide a greater cross link density as compared to some embodiments having a lesser concentration of catalyst. Additionally, the increased the gel time of the curable powder coating compositions can help provide that those compositions have greater surface wetting characteristics, as compared to some compositions having a relatively shorter gel time.

The curable powder coating compositions can have a $T_g$ of 50° C. to 80° C. and a product that is obtainable by curing the curable powder coating compositions can have a $T_g$ of 90° C. to 165° C.

For one or more embodiments, the curable powder coating compositions include an additive. Examples of the additive include, but are not limited to, fillers, pigments, dyes, stabilizers, flow modifiers, plastizisation agents, unreactive extender resins, plasticizers, accelerators, and combinations thereof.

EXAMPLES

Materials

D.E.R.™ 736 (aliphatic epoxy compound), available from The Dow Chemical Company.

1,8 diaza-bicyclo (5,4,0) undecene-7, (DBU), (catalyst), Chemical Abstracts Service (CAS) registry number 6674-22-2, available from Air Products and Chemicals, Inc.

ISONATE™ 50 O, P', (MDI), (diisocyanate), available from The Dow Chemical Company.

D.E.R.™ 330 (aromatic epoxy compound), available from The Dow Chemical Company.

XZ92457.02, (epoxy compound) available from The Dow Chemical Company.

Casamid 779, (amine and catalyst) available from Thomas Swan & Co. Ltd., U.K.

Titanium dioxide, ($TiO_2$), (pigment—Kronos 2310), available from Kronos Inc.

Barium sulfate, ($BaSO_4$), (filler—Blanc Fix EWO) available from Sachtleben.

Modaflow® III, (polyacrylate flow modifier) available from Cytec Industries Inc

Example 1

Oxazolidone Ring Containing Adduct

Three-hundred-ninety grams (g) of D.E.R.™ 736 were added to a flask and the flask contents were heated to 130° C. Two g of DBU were added to the flask over a period of time of about 60 seconds (s) and the flask contents were maintained at 145° C. Two-hundred-ten g of MDI were added to the flask over 60 min. and the temperature of the flask contents was maintained at a temperature from 160° C. to 170° C. The flask contents were maintained at a temperature of 165° C. for 15 min. A sample was taken and EEW was determined to be about 1450. Two-hundred-eighty g of D.E.R.™ 330 were added to the flask and the flask contents were maintained at a temperature from 140° C. to 150° C. One-hundred-twenty g of MDI were added to the flask over 60 min. and the temperature of the flask contents was maintained at a temperature from 170° C. to 175° C. The flask contents were maintained at a temperature of 165° C. for 15 min. to produce Example 1. Epoxide equivalent weight (EEW) was determined in grams/equivalent (g/Eq) by ASTM D1652, melt viscosity at 150° C. was determined in pascal second (Pa·s) by ASTM D3835, glass transition temperature ($T_g$) was determined in ° C. by ASTM D7028, and softening point was determined in ° C. by ASTM D6493, the results of which are shown in Table 1.

TABLE 1

|  | EEW (g/Eq) | Melt Viscosity (Pa·s) | $T_g$ (° C.) | Softening Point (° C.) |
|---|---|---|---|---|
| Example 1 | 981 | 7.0 | 42 | 97 |

Comparative Example A

Two-thousand-eight-hundred-fifty g of D.E.R.™ 736, 500 g of D.E.R.™ 330 were added to a flask and heated to 130° C. under a nitrogen atmosphere. Ten g of DBU was added to the flask and the flask contents were heated to 145° C. One-thousand-six-hundred-fifty g of MDI were added to the flask portion by portion over 120 min. while the contents of the flask were maintained at a temperature of 170° C. to 175° C. After addition of the MDI, the contents of the flask were maintained at a temperature of 165° C. for 15 min. to produce Comparative Example A, where D.E.R.™ 736 (aliphatic epoxy) and D.E.R.™ 330 (aromatic epoxy) were reacted with MDI in a one step process. The EEW, melt viscosity at 150° C., $T_g$, and softening point were determined by the test methods described for Example 1, the results of which are shown in Table 2.

TABLE 2

|  | EEW (g/Eq) | Melt Viscosity (Pa·s) | $T_g$ (° C.) | Softening Point (° C.) |
|---|---|---|---|---|
| Comparative Example A | 1156 | 4.2 | 20 | 74 |

Comparative Example B

Six-hundred-forty-five g of D.E.R.™ 736 were added to a flask and the flask contents were heated to 130° C. Two g of DBU were added to the flask and the flask contents were heated to 145° C. Three-hundred-fifty-five g of MDI were added to the flask portion by portion over 60 min. and the temperature of the flask contents was maintained at a temperature from 160° C. to 170° C. The flask contents were maintained at a temperature of 165° C. for 15 min. to produce Comparative Example B. The EEW, melt viscosity at 150° C., $T_g$, and softening point were determined by the test methods described for Example 1, the results of which are shown in Table 3.

TABLE 3

| | EEW (g/Eq) | Melt Viscosity (Pa · s) | $T_g$ (° C.) | Softening Point (° C.) |
|---|---|---|---|---|
| Comparative Example B | 1488 | 3.2 | 23 | 71 |

The data in Tables 1 through 3 shows that Example 1 has a higher glass transition temperature and softening point than either Comparative Example A or Comparative Example B. The relatively higher glass transition temperature and softening point of Example 1 helps provide a reduced propensity for sintering as compared to Comparative Example A and Comparative Example B, which will sinter at relatively lower temperatures.

Examples 2 through 4, which were curable powder coating compositions, and Comparative Example C, which was an epoxy system, were formed by combining the components shown in Table 4 and Table 5, respectively.

TABLE 4

| Component | Example 2 (curable powder coating composition) | Example 3 (curable powder coating composition) | Example 4 (curable powder coating composition) |
|---|---|---|---|
| XZ92457.02 (g) (epoxy compound) | 737.2 | 698.4 | 659.6 |
| Example 1 (g) (oxazolidone ring containing adduct) | 38.8 | 77.6 | 116.4 |
| Casamid 779 (g) (amine and catalyst) | 35 | 35 | 35 |
| TiO$_2$ (g) (pigment) | 50 | 50 | 50 |
| BaSO$_4$ (g) (filler) | 140 | 140 | 140 |
| Modaflow ® III (g) (polyacrylate flow modifier) | 10 | 10 | 10 |

TABLE 5

| Component | Comparative Example C |
|---|---|
| XZ92457.02 (g) (epoxy compound) | 776.0 |
| Casamid 779 (g) (amine and catalyst) | 35 |
| TiO$_2$ (g) (pigment) | 50 |
| BaSO$_4$ (g) (filler) | 140 |
| Modaflow ® III (g) (polyacrylate flow modifier) | 10 |

Some properties of Examples 2 through 4 and Comparative Example C were determined. The gel time was determined by CAN/CSA-Z245.20-M92, the powder $T_g$, the coating $T_g$ and the peak cure temperature were determined by differential scanning calorimetry. Table 6 and Table 7 shows the results for Examples 2 through 4 and Comparative Example C, respectively.

TABLE 6

| Property | Example 3 (curable powder coating composition) | Example 4 (curable powder coating composition) | Example 5 (curable powder coating composition) |
|---|---|---|---|
| Gel time (s) | 59 | 67 | 72 |
| Tg powder (° C.) | 61 | 61 | 61 |
| Tg coating (° C.) | 157 | 150 | 143 |
| Peak cure T (° C.) | 180 | 172 | 175 |

TABLE 7

| Property | Comparative Example 3 |
|---|---|
| Gel time (s) | 54 |
| Tg powder (° C.) | 60 |
| Tg coating (° C.) | 162 |
| Peak cure T (° C.) | 168 |

The gel time can be correlated to a reactivity such that a relatively lower gel time corresponds to a relatively greater reactivity. For some applications a gel time of 40 s to 120 s is advantageous. The data of Table 6 shows that the gel time, and thus the reactivity, of Examples 2 through 4 is advantageous for those applications.

Examples 2 through 4 and Comparative Example C were sprayed onto pre-heated 6mm steel panels, post-cured for 3 min. at 235° C., and water quenched to about 20° C. The spraying, curing, and quenching resulted in panels having coatings of various thicknesses measured in micrometers (μm). Examples 2 through 4 provided Examples 5 through 8 respectively. Examples 5 through 8 were products obtained by curing the curable powder coating compositions, Examples 2 through 4 respectively. Likewise, Comparative Example C provided Comparative Example D. The coated panels were stored at −30° C. for 24 hours. The coated panels were tested following procedures in CAN/CSA-Z245.20-M92. The coated panels were rated by bending. The ratings were on a scale from 1 being the most flexible to 4 being the least flexible. Rating 1 indicated no damage to the coating was observed, rating 2 indicated multiple small (1 cm length) cracks in coating were observed, rating 3 indicated one large crack in the coating was observed, and rating 4 indicated multiple large cracks in the coating were observed. Table 8 and Table 9 show the respective results of bending the coated panels.

TABLE 8

| Example 5 | | Example 6 | | Example 7 | |
|---|---|---|---|---|---|
| Coating thickness (μm) | Bend rating | Coating thickness (μm) | Bend rating | Coating thickness (μm) | Bend rating |
| 406 ± 25 | 3 | 400 ± 36 | 1 | 356 ± 29 | 2 |
| 418 ± 25 | 4 | 437 ± 37 | 1 | 424 ± 33 | 2 |
| 424 ± 48 | 4 | 461 ± 60 | 3 | 454 ± 21 | 2 |
| — | — | 490 ± 30 | 3 | 463 ± 44 | 2 |

TABLE 9

| | Comparative Example D | |
|---|---|---|
| Coating thickness (μm) | | Bend rating |
| 378 ± 27 | | 4 |
| 464 ± 25 | | 4 |
| 569 ± 29 | | 1 |
| 594 ± 38 | | 2 |

The data of Table 8 and Table 9 indicates that the bending characteristics of the coated panels are improved by employing the oxazolidone ring containing adducts. Particularly the bending characteristics for Example 6 and Example 7, where the ratings of 4 which corresponded to Comparative Example D were improved to ratings of 1 or 2 respectively. These improved bending characteristics show that the oxazolidone ring containing adducts are useful as flexibilizers.

What is claimed:

1. A curable powder coating composition comprising a resin component and a hardener component, where the hardener component is selected from the group consisting of amines, anhydrides, carboxyl-functional polyesters, and combinations thereof, where the resin component includes an oxazolidone ring containing adduct formed by a method, comprising:

reacting an aliphatic epoxy compound, a first diisocyanate and a catalyst to form a first adduct, wherein the aliphatic epoxy compound is a polyglycidyl ether of aliphatic polyols or alkylene-oxide adducts thereof; and reacting a second diisocyanate with a mixture of the first adduct and an aromatic epoxy compound to form the oxazolidone ring containing adduct, wherein where the aliphatic epoxy compound is 20 weight percent (wt %) to 60 wt % of a total weight of the oxazolidone ring containing adduct, the aromatic epoxy compound is 20 wt % to 40 wt % of the total weight of the oxazolidone ring containing adduct, and the first and second diisocyanate are 10 wt % to 40 wt % of the total weight of the oxazolidone ring containing adduct such that the aliphatic epoxy compound, the aromatic epoxy compound, and the diisocyanate weight percents sum to 100 wt % of the oxazolidone ring containing adduct.

2. The curable powder coating composition of claim 1, where the oxazolidone ring containing adduct has an epoxide equivalent weight of 800 grams/equivalent (g/eq) to 1300 g/eq, a melt viscosity at 150 degrees Celcius (° C.) of 2 pascal second (Pa·s) to 10 Pa·s, a softening point of 80° C. to 100° C. and a glass transition temperature of 35° C. to 55° C.

3. The curable powder coating composition of claim 1, where the aliphatic epoxy compound is selected from the group consisting of a diglycidyl ether of polypropylene glycol, 1,4-butanediol diglycidyl ether, 1,6-hexanediol diglycidyl ether, and combinations thereof; the aromatic epoxy compound is selected from the group consisting of a glycidyl ether of bisphenol A, a glycidyl ether of bisphenol F, and combinations thereof; and the first and second diisocyanates are each selected from the group consisting of 4,4'-diphenylmethane diisocyanate, toluene diisocyanate, isophorone diisocyanate, 4,4'-methylenebis(cyclohexylisocyanate), and combinations thereof.

* * * * *